US009265797B2

(12) United States Patent
Al-Ardah et al.

(10) Patent No.: US 9,265,797 B2
(45) Date of Patent: Feb. 23, 2016

(54) SURGICAL TECHNIQUE FOR HARVESTING AUTOGENOUS MANDIBULAR SYMPHYSIS GRAFT

(71) Applicants: Aladdin J Al-Ardah, St. Loma Linda, CA (US); Fawaz Alqahtani, Alkharj (SA); Jaime L. Lozada, St. Loma Linda, CA (US)

(72) Inventors: Aladdin J Al-Ardah, St. Loma Linda, CA (US); Fawaz Alqahtani, Alkharj (SA); Jaime L. Lozada, St. Loma Linda, CA (US)

( * ) Notice: Subject to any disclaimer, the term of this patent is extended or adjusted under 35 U.S.C. 154(b) by 194 days.

(21) Appl. No.: 14/086,766

(22) Filed: Nov. 21, 2013

(65) Prior Publication Data

US 2015/0140651 A1 May 21, 2015

(51) Int. Cl.
- *A61K 35/32* (2015.01)
- *A61B 17/16* (2006.01)

(52) U.S. Cl.
CPC ............. *A61K 35/32* (2013.01); *A61B 17/1635* (2013.01)

(58) Field of Classification Search
IPC ................ A61K 35/32; A61B 17/1635,17/1673
See application file for complete search history.

(56) References Cited

U.S. PATENT DOCUMENTS

| 5,350,382 A | 9/1994 | Armstrong |
| 5,954,671 A | 9/1999 | O'Neill |
| 2006/0025796 A1 | 2/2006 | Merced-O'Neill |

OTHER PUBLICATIONS

Cranin et al, "Autogenous Bone Ridge Augmentation Using the Mandibular Symphysis as a Donor", Journal of Oral Implantology, 2001, vol. 27, No. 1, pp. 43-47.*

Desai et al, "Current Concepts and Guidelines in Chin Graft Harvesting: A literature review." International Journal of Oral Health Sciences, Jan.-Jun. 2013, vol. 3, Issue 1, pp. 16-25.*

Gungormus et al, "Evaluation of the Mandible as an Alternative Autogenous Bone Source for Oral and Maxillofacial Reconstruction." The Journal of International Medical Research, 2002, vol. 30, pp. 260-264.*

"Muscles of the Face (Facial Muscles)"—Medical Illustration. Nucleus Medical Media, Medical Illustration. Retrieved from http:// http://www.nucleuscatalog.com/muscles-of-the-face-facial-muscles/view-item?ItemID=9300 on Jul. 28, 2015.*

Tecimer et al, "The Use of Autogenous Bone Grafting to Reconstruct a Mandibular Knife Edge Ridge Before Implant Surgery: A Case Report." Journal of Oral Implantology, 2001, vol. 27, No. 2, pp. 98-102.*

Toscano et al, "The Art of Block Grafting A Review of the Surgical Protocol for Reconstruction of Alveolar Ridge Deficiency." The Journal of Implant & Advanced Clinical Dentistry, Mar. 2010, vol. 2, No. 2, pp. 45-66.*

Michael Peleg, DMD, et al. "Maxillary Sinus and Ridge Augmentations Using a Surface-Derived Autogenous Bone Graft", American Association of Oral and Maxillofacial Surgeons, pp. 1535-1544. (2004).

Marina Gabriela Monteiro, et al. "Cerclagem com abracadeira de náilon ou de fib de aco no reparo de fraturas experimentais de sinfise mandibular em gatos", Acta Scientae Veterinariae, 38(4), pp. 363-369. (2010).

Stig A. Ellingsen, et al. "MASTEROPPGAVE: Bone Modifying techniques in the anterior maxilla prior to implant placement—A literature review", Universitetet Tromsø, Det Helsevitenskapelige Fakultet, Institute for Klinisk Odontologi, pp. 1-34. (Jun. 2012).

* cited by examiner

*Primary Examiner* — Allison Fox
(74) *Attorney, Agent, or Firm* — Oblon, McClelland, Maier & Neustadt, L.L.P.

(57) ABSTRACT

A surgical technique for harvesting an autogenous symphysis bone graft including making a single vertical incision to the symphysis area of a patient and harvesting bone from the symphysis area of the patient's mandible. The single vertical incision is made parallel to muscle fibers of the patient's chin.

9 Claims, 26 Drawing Sheets

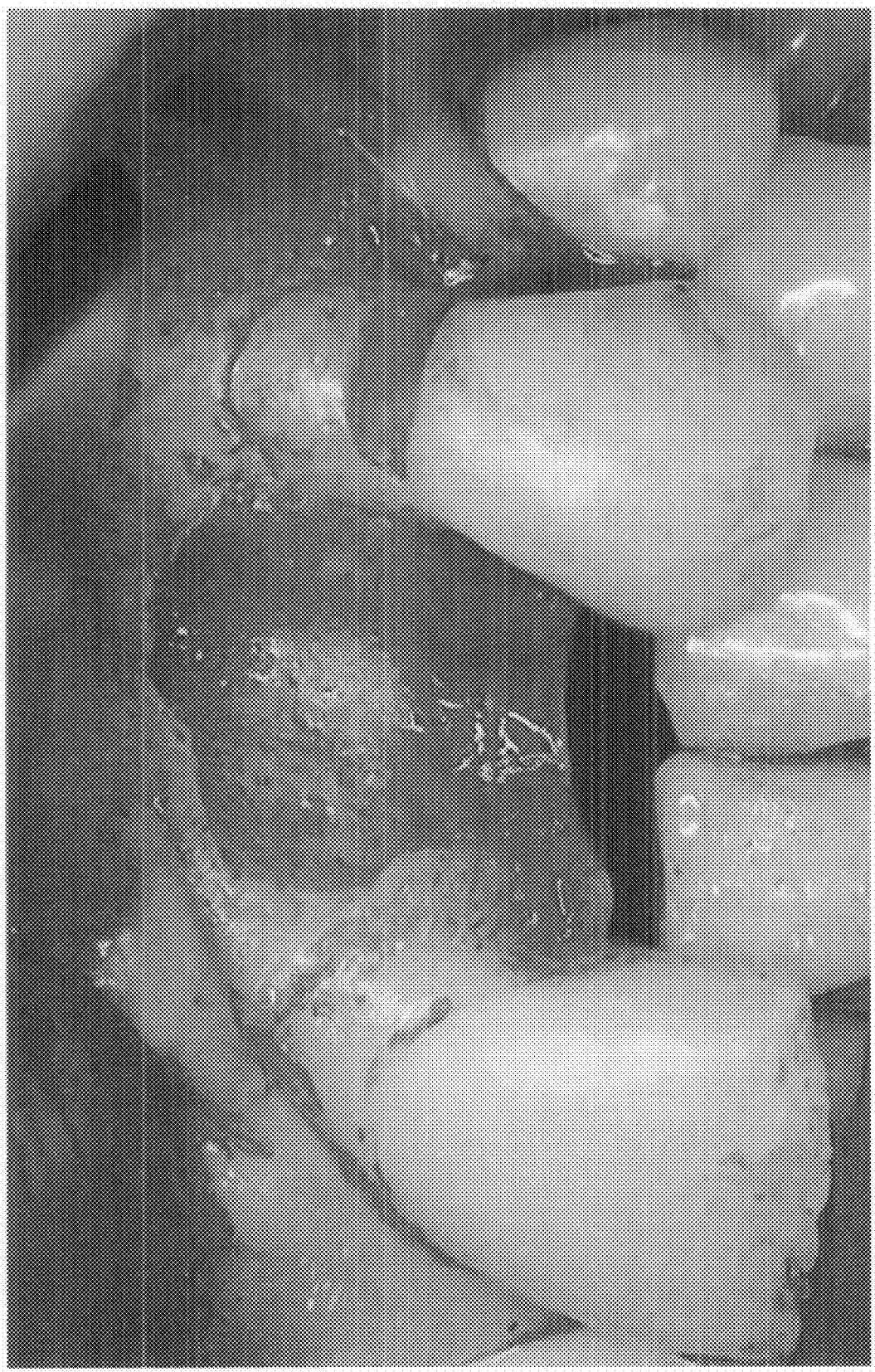

SURGICAL TECHNIQUE FOR HARVESTING AUTOGENOUS MANDIBULAR SYMPHYSIS GRAFT

GRANT OF NON-EXCLUSIVE RIGHT

This application was prepared with financial support from the Saudia Arabian Cultural Mission, and in consideration therefore the present inventor(s) has granted The Kingdom of Saudi Arabia a non-exclusive right to practice the present invention.

BACKGROUND OF THE INVENTION

1. Field of the Disclosure

The disclosure includes a process for immediate implant placement and provisionalization of a maxillary lateral incisor with a chronic buccal infection and a defective buccal plate including harvesting autogenous bone from the mandibular symphysis area with a single vertical incision.

2. Description of the Related Art

Restoration in the anterior region of the mouth is challenging both from the surgical and prosthetic point of view. The goal of implant therapy today is not only to attain osseointegration of the implant but also to enhance and maintain the soft tissue esthetics around dental implants. Maintenance of the soft tissue architecture around the implant restoration to mimic the contra lateral tooth in the anterior esthetic area is a requirement for a successful restoration. Immediate implant placement and loading maintains the soft and hard tissue architectures, avoid need for additional surgeries, and shorten treatment time (Chen S T, Wilson T G Jr, Hammerle C H, "Immediate or early placement of implants following tooth extraction: Review of biologic basis, clinical procedures, and outcomes," Int. J. Oral Maxillofac Implants. 2004; 19 (suppl): 12-25; Koh R U, Rudek I, Wang H L, "Immediate implant placement: positives and negatives," Implant Dent., 2010 April, 19(2):98-108; and Lazzara R J, "Immediate implant placement into extraction sites: Surgical and restorative advantages," Int. J. Periodontics Restorative Dent., 1989; 9:332-343—incorporated herein by reference). Clinical trials showed that a high success rate of the immediate implant placement in fresh extraction alveolus (Kan J Y, Rungcharassaeng K., "Immediate placement and provisionalization of maxillary anterior single implants: a surgical and prosthodontic rationale," Pract. Periodontics Aesthet. Dent., 2000: 12(9): 817-24; Botticelli D, Berglundh T, Lindhe J., "Hard-tissue alterations following immediate implant placement in extraction sites," J. Clin. Periodontol, 2004: 3 1:820-828; Chen S T, Darby I B, Reynolds E C, "A prospective study of non-submerged immediate implants: clinical outcomes and esthetic results," Clin. Oral Impl. Res., 2007; 18:552-5623—incorporated herein by reference). Careful analysis of soft and hard tissue is prerequisite for an immediate implant placement in the anterior region of the mouth (Kois J C, Kan J Y., "Predictable peri-implant gingival aesthetics: surgical and prosthodontic rationales," Pract. Proced. Aesthet. Dent., 2001; 13(9): 691-8—incorporated herein by reference). Kois named five diagnostic factors used to assist a predictable immediate implant placement (Kois J C., "Predictable single-tooth peri-implant esthetics: Five diagnostic keys," Compend. Contin. Educ. Dent., 2004: 25:895-896, 898, 900 passim; quiz 906-897—incorporated herein by reference). Three of five diagnostic factors are the form, biotype of the periodontium and the height of the alveolar crest prior to the tooth extraction which addressed the importance of soft and hard tissue components. Presence of a chronic apical or peri-odontal infected residual socket may be considered as a contraindication for the immediate implant placements (Schwartz-Arad D, Chaushu G. Placement of implants into fresh extraction sites: 4 to 7 years retrospective evaluation of 95 immediate implants. J Periodontol 1997; 68:1110-1116—incorporated herein by reference). An infected alveolus confirms the presence of the bacteria that will induce inflammatory activity, increase the bone resorptive process and result in a higher risk of implant failure (Campos M I, dos Santos M C, Trevilatto P C, Scarel-Caminaga R M, Bezerra F J, Line S R., "Early failure of dental implants and TNF-alpha (G-308A) gene polymorphism," Implant Dent. 2004; 13:95-101—incorporated herein by reference). Lindeboom et al. compared the survival rate of immediate and delayed implant placement into infected residual alveolus (Lindeboom J A, Tjiook Y, Kroon F H., "Immediate placement of implants in periapical infected sites: A prospective randomized study in 50 patients," Oral Surg. Oral Med. Oral Pathol. Oral Radiol. Endod., 2006; 101:705-710—incorporated herein by reference). The author showed a 92% survival rate of immediately placed implants compared with a 100% survival rate of delayed placement implants. Additionally, there was more mid-buccal soft tissue recession in the immediate placement compared with the delayed placement protocol one year after placement. In another study by Seigenthaler et al. demonstrated an equal survival rate of the immediate and delayed implant placement into infected socket (Siegenthaler D W, Jung R E, Holderegger C, Roos M, Hammerle C H., "Replacement of teeth exhibiting periapical pathology by immediate implants: A prospective, controlled clinical trial," Clin. Oral Implants Res., 2007; 18:727-737—incorporated herein by reference). Complete debridement of the alveolus with a primary stability of the implant is prerequisite for immediate placement. Immediate placement of an implant in presence of a chronic infection with a deficient buccal plate in a patient with a high smile line is very challenging and complex. Autogenous bone graft harvested from intraoral or extraoral sites has been used for predictable guided bone regeneration (Misch C M, Misch C E., "The repair of localized severe ridge defects for implant placement using mandibular bone grafts," Implant. Dent., 1995 Winter; 4(4):261-7; and Pikos M A., "Mandibular block autografts for alveolar ridge augmentation," Atlas Oral Maxillofacial Surg. Clin. N. Am., 2005; (13):91-107—incorporated herein by reference). There are certain complications of the donor sites have been reported (Toscano N J, Shumaker N, Holtzclaw D H., "The Art of Block Grafting: A review of the surgical protocol for reconstruction of alveolar ridge deficiency," J. Implant. Adv. Clin. Dent., 2010; Vol. 2, No. 2; Misch C M., "Comparison of intraoral donor sites for onlay grafting prior to implant placement," Int. J. Oral. Maxillofac. Implants, 1997; 12:767-776—incorporated herein by reference).

A surgical process and the restorative protocol for an immediate implant placement and provisionalization in the presence of large periodontal abscess with a buccal plate defect in a highly esthetic demanding area is described by harvesting an autogenous mandibular symphysis graft harvested with a single vertical incision.

Autegenous bone graft has been used as a gold standard for grafting procedure due to the osteogenic, osteoinductive, and osteioconductive capacity. Intraoral harvested bone from mandibular symphysis can be used for predictable guided bone regeneration (GBR). The increase of popularity of using the mandibular symphysis as a donor site is due to the Local availability of the donor sites eliminate need for extraoral sources, up to 10 cc of Cortico:cancelious bone graft can be harvested, and a predictable bony gain up to 6 mm in horizontal and vertical dimensions. However, while the mandibular symphysis has many advantages, there are some complications of using such technique making it less attractive for dental practitioners. Post-operative morbidity and patient discomfort have been reported as a major concern of harvesting bone from the mandibular symphysis. Misch reported that 29% of patients reported alter lower incisors sensation, 9.6% had a paresthesia for up to six months, and 10.7% had incision dehiscence at the donor site. Chin ptosis is also a concern due to the disturbance of the muscle attachments due to bone harvesting from the mandibular symphysis area.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

In one aspect the present disclosure describes a surgical technique for implant placement and provisionalization of an incisor that includes harvesting autogenous bone.

In another embodiment the disclosure includes harvesting autogenous bone from a mandibular symphysis area.

In a further embodiment of the disclosure autogenous bone is harvested from a mandibular symphysis area with a single vertical surgical incision.

In a further embodiment of the invention a single vertical incision is used to harvest autogenous bone from a mandibular symphysis area using an incision parallel to muscle fibers of a patient's chin.

In a further embodiment of the invention a single vertical incision is made to a patient's chin without muscular detachment.

In a further embodiment of the invention harvested bone from a symphysis area is used to generate a defected area in an oral cavity.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 5: Tetracycline antibiotic application;
FIG. 8b: Incision design for Symphysis donor site;
FIG. 9: Anterior maxillary recipient site defect after complete debridement of the lesion.

DETAILED DESCRIPTION OF THE INVENTION

Figure 1:
FIG. 1: Periapical radiograph of tooth #10, January 2003.

Referring now to the drawings, wherein like reference numerals designate identical or corresponding parts throughout the several views.

Autogenous bone grafting includes harvesting bone from a single individual and returning the bone to the donor. Autogenous bone grafting is used to enhance bone volume in the maxilla and/or mandible before implantation of a device or a replacement tooth. Autogenous bone grafting may also be used for reconstructive purposes, for example, where bone has been compromised due to bacterial infection, degeneration or trauma.

Conventional autogenous bone grafting utilizes bone harvested from various areas of the body and mouth. For example, bone may be harvested from the tibia, fibula, scapula, ribs and from portions of the mouth. In the present invention bone harvesting occurs from the maxilla or mandible of a patient. Preferably autogenous bone harvesting is carried out in a single treatment protocol with bone grafting and/or placement of an implant.

Preferably the harvested bone graft is oversized such that it may fully accommodate the area for implant and/or reconstruction. Any overage in harvested bone may be trimmed for a more precise fit. In another embodiment of the invention one or more of bone marrow and cancellous bone is combined with the autogenous bone graft. The bone marrow and/or cancellous bone may be packed into a bone cavity prior to or concurrently with the autogenous bone graft. Preferably the autogenous bone graft is the outermost portion of the implant area.

EXAMPLE

Figure 2:
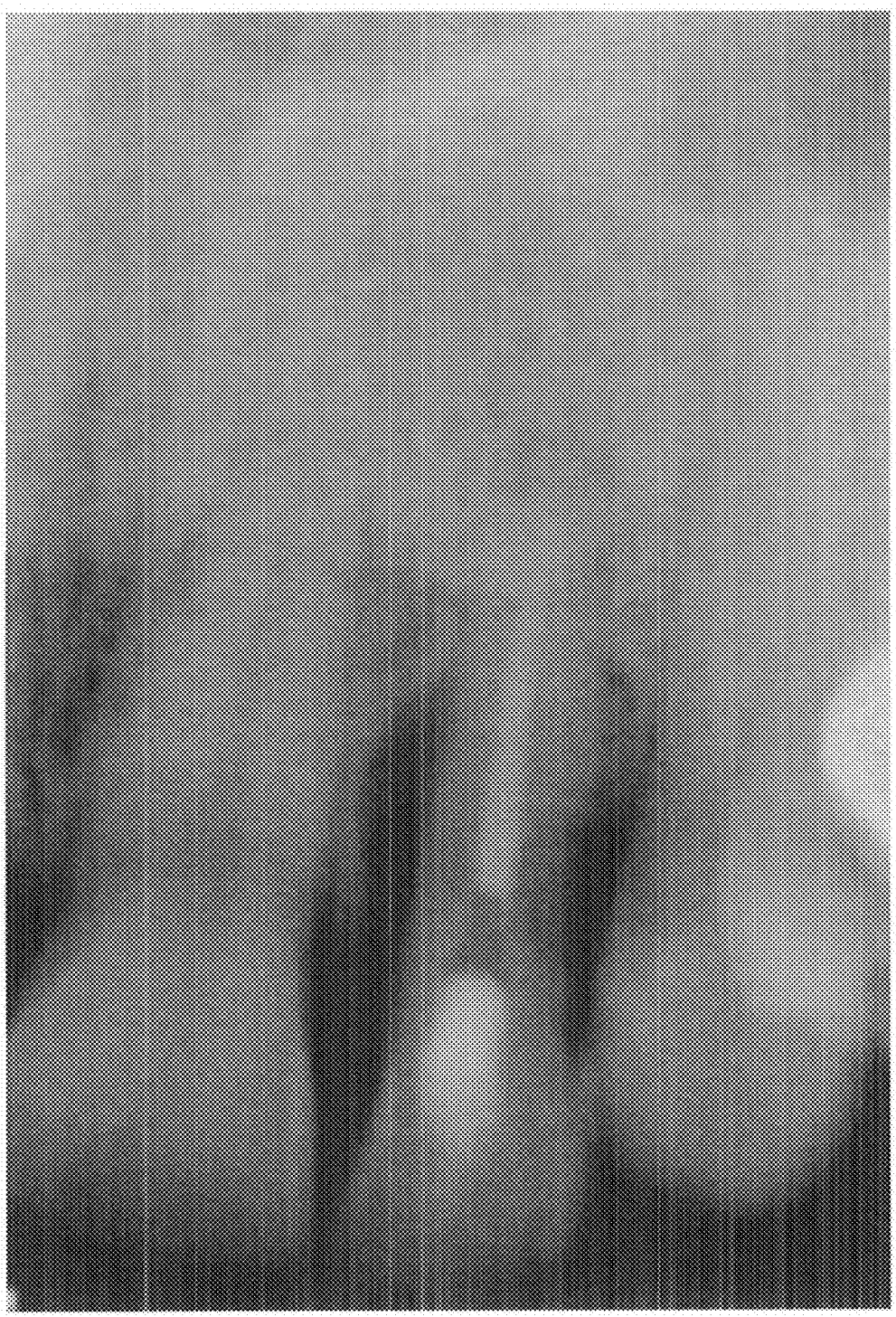
FIG. 2: Periapical radiograph of tooth #10, August, 2003.

This patient is a 43 years old Caucasian female who was referred to the Center for Implant Dentistry at Loma Linda University dental school. Her chief complaint was "I have had an infection in my upper front tooth for more than seven months". A lesion with a buccal fistula track and purulent discharge started on tooth #10 in January 2003. The diagnosis was a localized periodontal abscess (FIG. 1). Scaling and root planning was performed and the patient was placed on systemic antibiotics; Amoxicillin 500 mg (1 cap q8 hrs for 1 week) and Clidamycin 300 mg (1 tab q6 hrs for 1 week) on separate occasions. The exudate ceased while the patient was taking the antibiotic and would return shortly after the antibiotic course was finished. The patient was transferred from the periodontic department to the endodontic department for a pulpal evaluation. The diagnosis was a primary endodontic lesion with secondary periodontal involvement. Pulpectomy and root canal treatment was performed using MTA material. Patient was under endodontic evaluation for six months (FIG. 2). The lesion did not respond to any further antibiotic treatment. In September 2003, the patient was transferred to the implant department for possible implant placement in area of tooth #10. Review of the patient's medical history revealed that patient had no medical contraindications to surgical and prosthodontic treatment. The patient admits to have two alcohol cocktails per day with no history of smoking. The Patient is not aware of any parafunctional oral habits and oral hygiene regimen consists of brushing twice a day with flossing.

Figure 3:
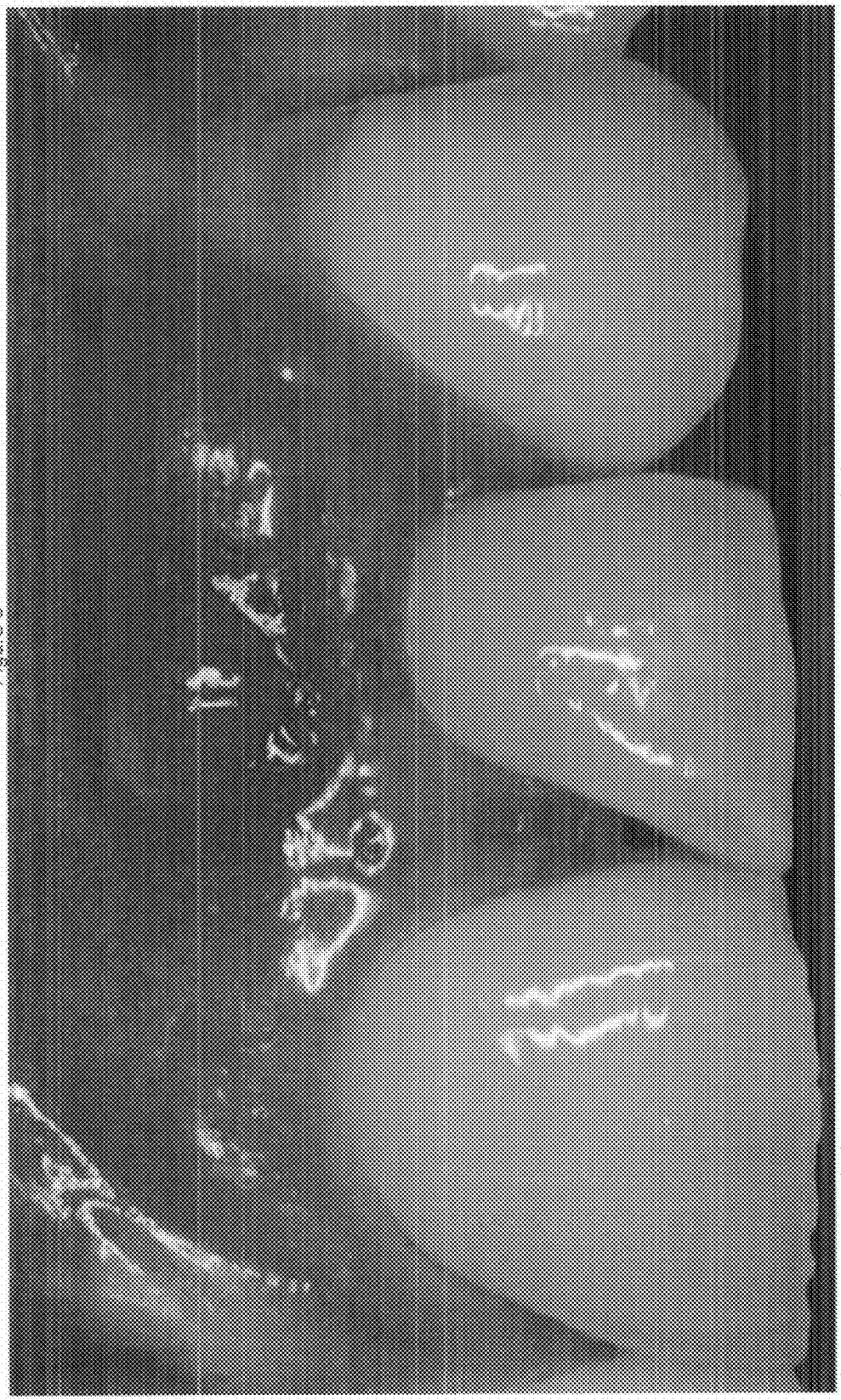
FIG. 3: Pretreatment frontal view.
Figure 4A:
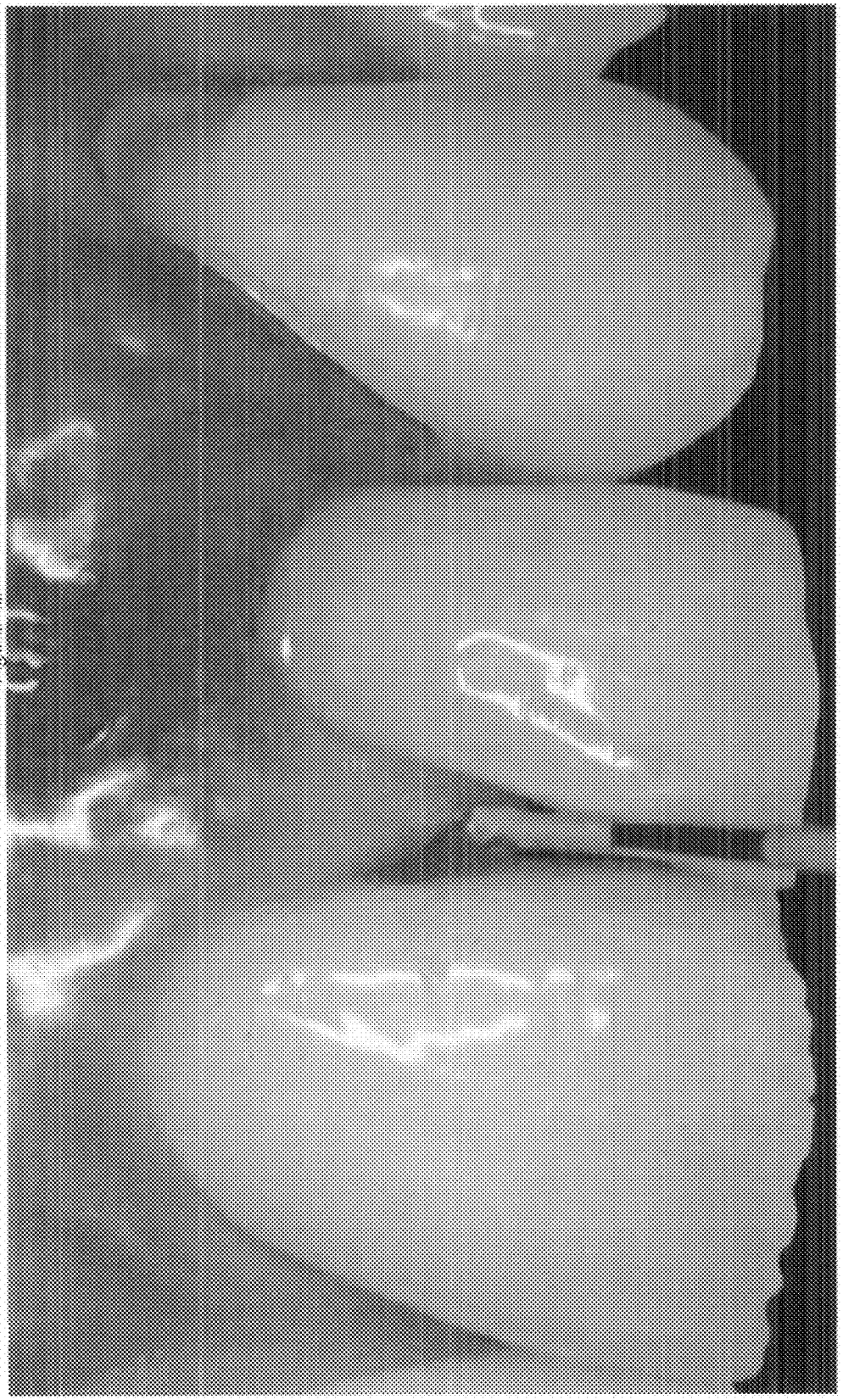
FIG. 4a: Bone sounding, distal of tooth #9.
Figure 4B:
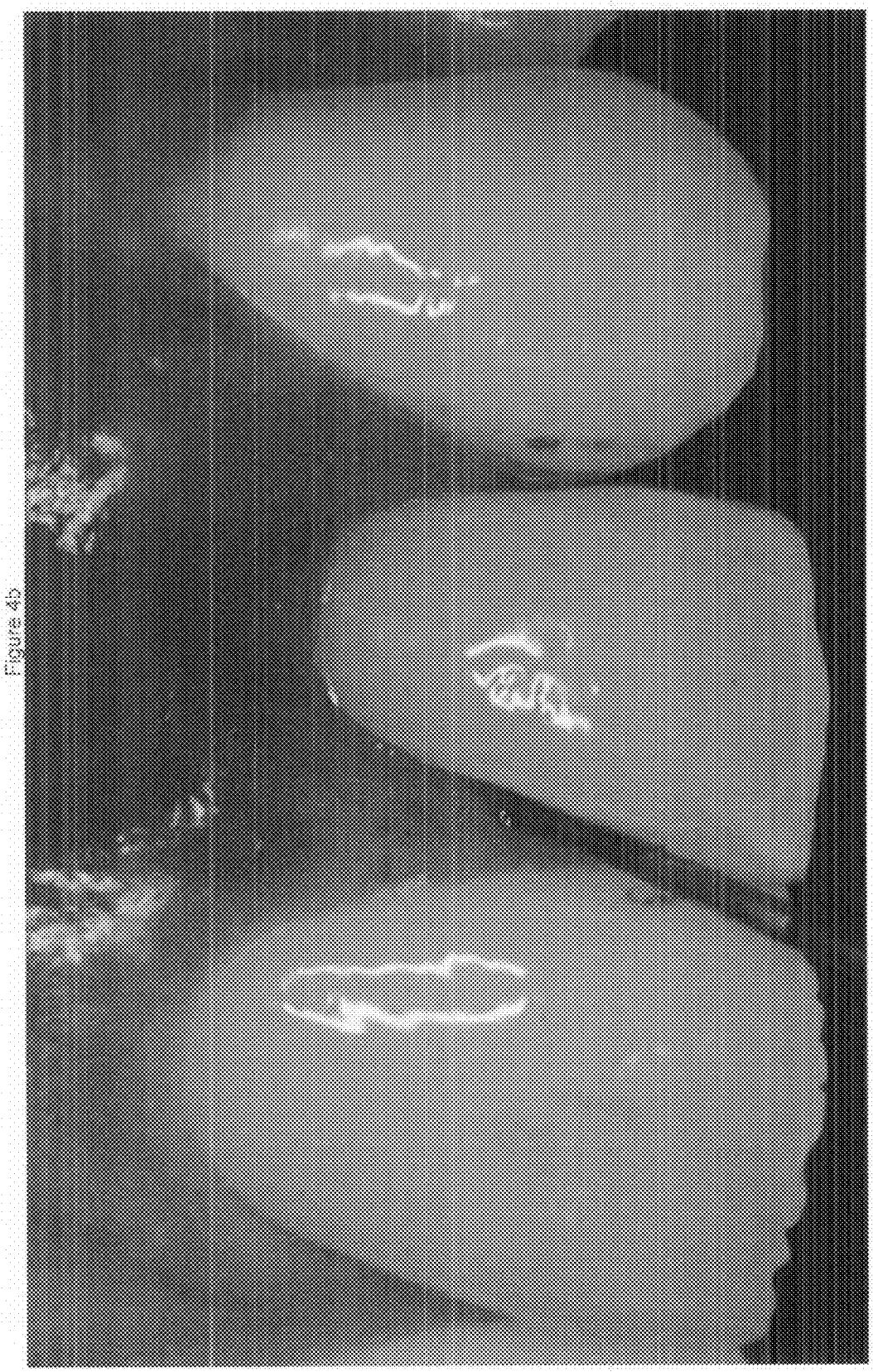
FIG. 4b: Pretreatment bone sounding, mesial of tooth #10.
Figure 4C:
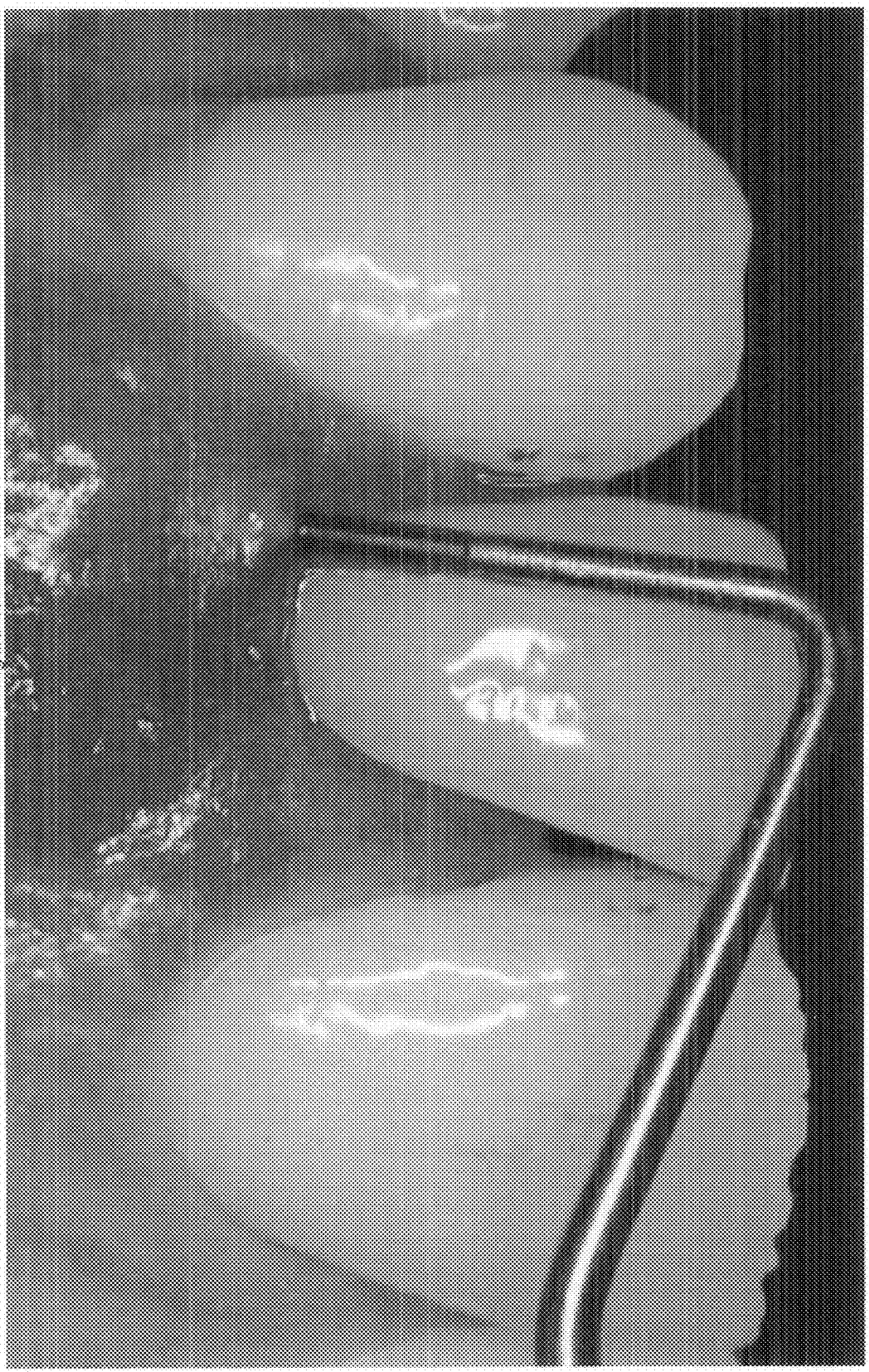
FIG. 4c: Bone sounding, distobuccal of tooth #10.
Figure 4G:
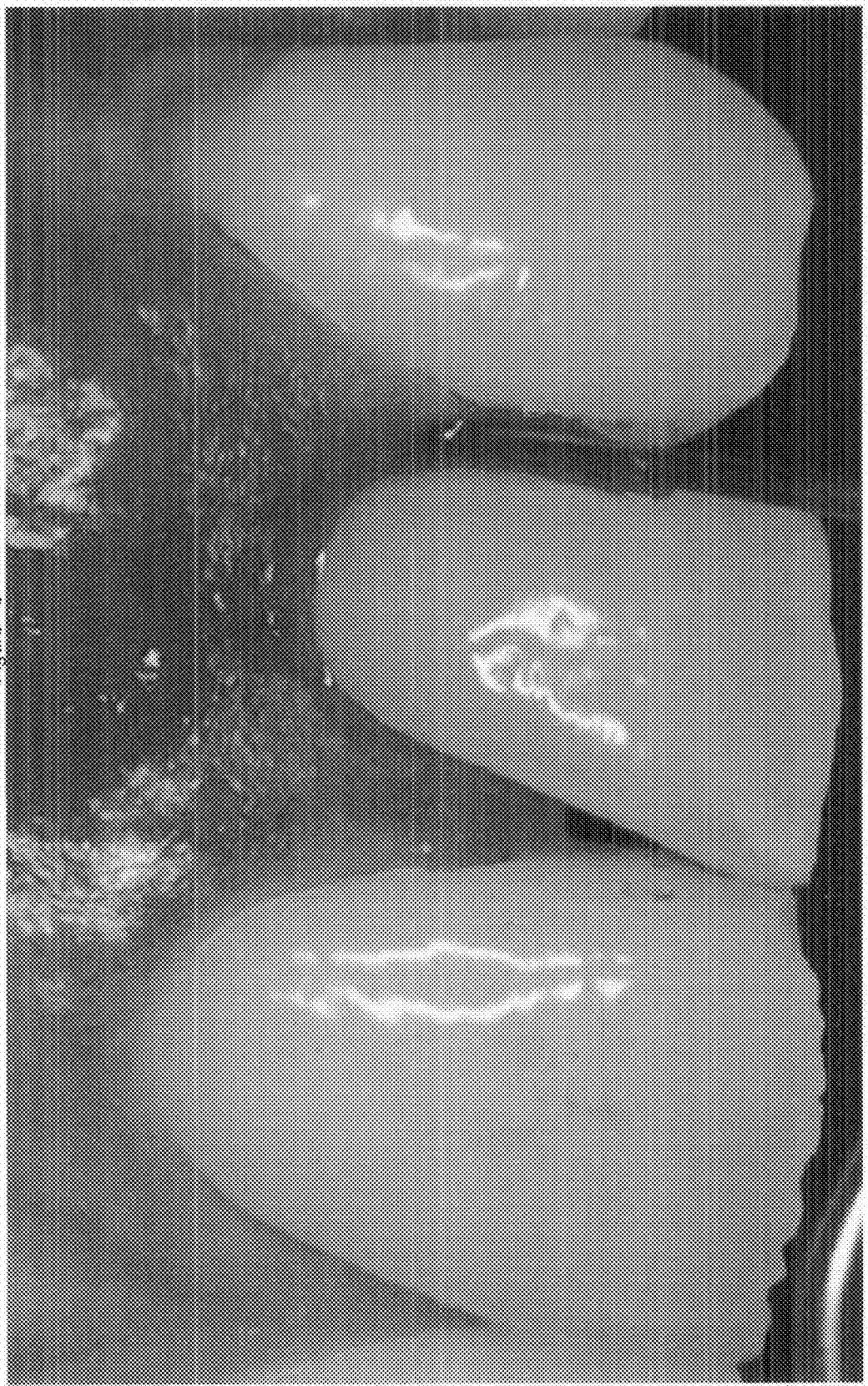
FIG. 4d: Bone sounding, distal of tooth #10.
FIG. 4e: Bone sounding, mesial of tooth #11.
Figure 4E:
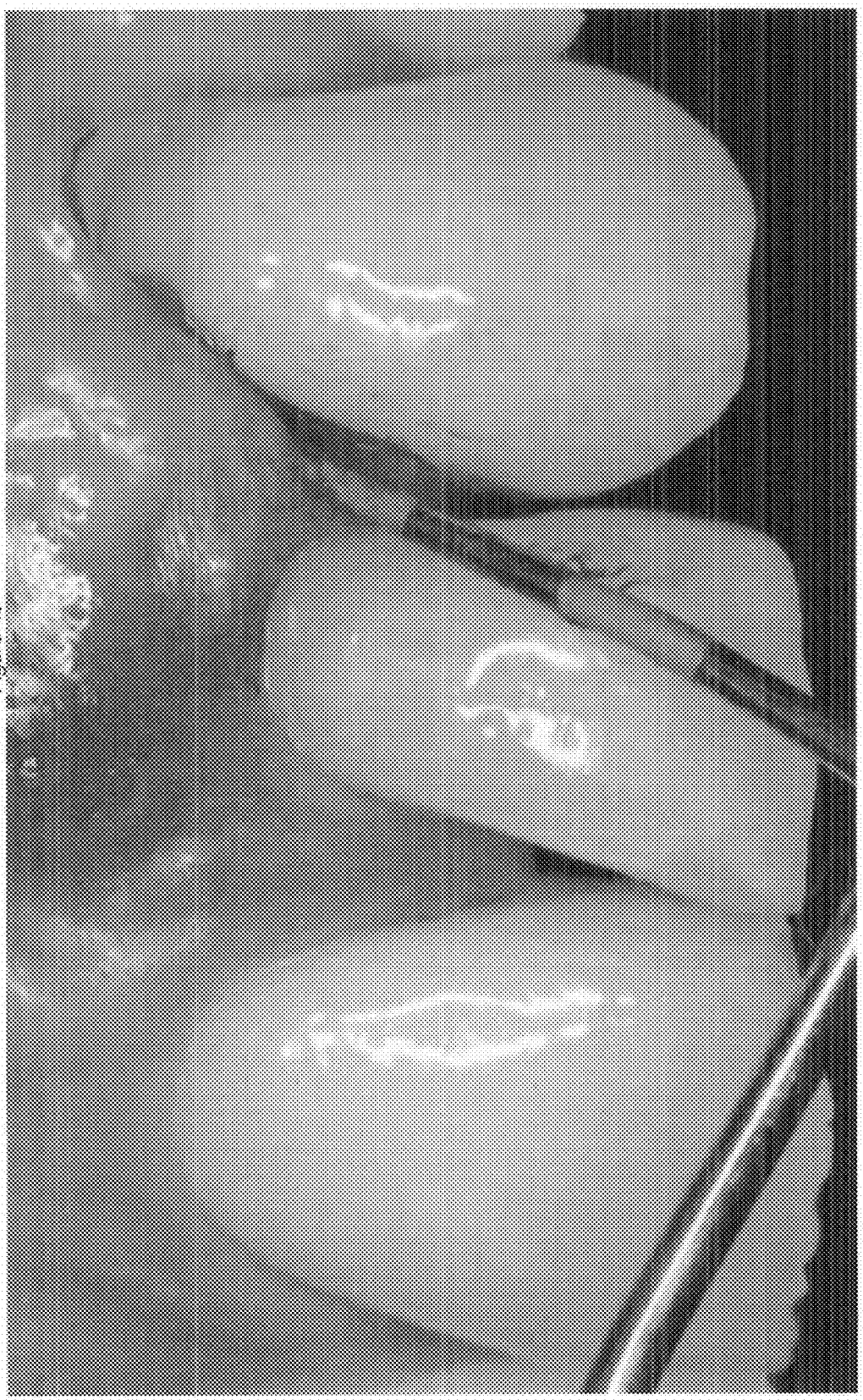

Clinical examination of tooth #10 revealed that there is no mobility and no pain on stick biting. The soft tissue evaluation revealed buccal fistula with a discharge buccal to tooth #10 (FIG. 3). Two periapical radiographs taken in different angles showed a buccal bone defect that has progressed considerably compared to the periapical radiograph made at the initial exam. The initial impression was a persistent chronic periodontal abscess due to a possible root fracture. The patient selected an implant to replace the fractured tooth. Upon clinical exam the patient presents a thin gingival biotype. The mesial and distal papilla scored grade 2 according to interdental papilla loss classification (Jemt T., "Regeneration of gingival papillae after single-implant treatment," Int. J. Periodontics Restorative Dent., 1997 August; 17(4): 326-33—incorporated herein by reference). The bone sounding was as follow; 3 mm on distal of tooth #9, 9 mm on mesial of tooth #10, 7 mm on mid-buccal and 10 mm on distal of tooth #10; and 3.5 mm on mesial of tooth #11. The tooth shape was triangular (FIG. 4). The patient has a high smile line with a symmetrical gingival zenith.

The dilemma exists if the extraction and bone graft were performed first and then delayed implant placement, which could lead to a hard and soft tissue changes Immediate implant placement and provisionalization will preserve the soft tissue contour, however the buccal abscess has not been responsive to systemic antibiotics and may complicate the implant placement stability and jeopardize the bone graft needed to repair the buccal defect.

Procedure in Detail

Figure 6:
FIG. 6: Microbial sample for culture test.
Figure 6:
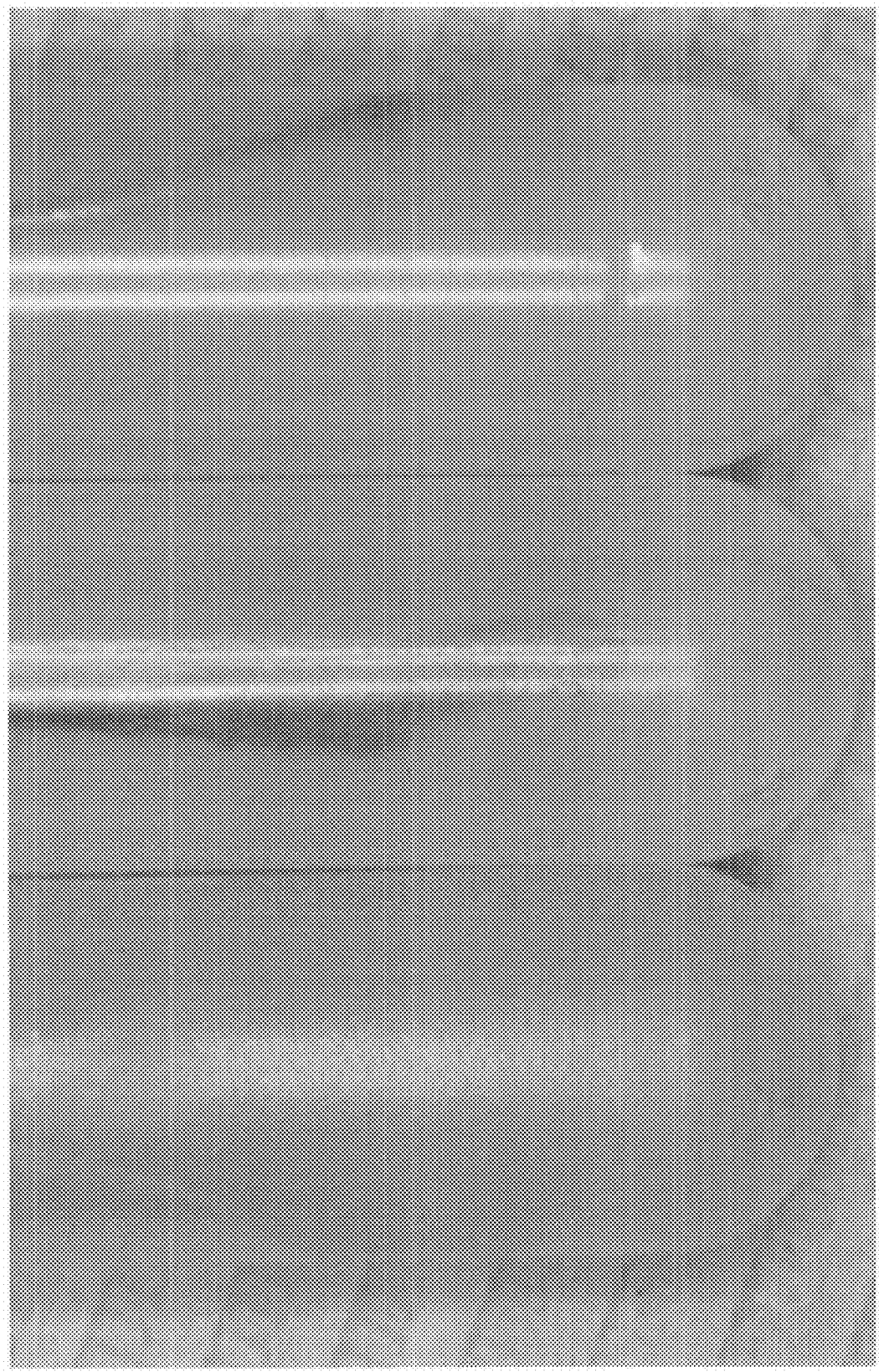

Local application of a tetracycline antibiotic (500 mg diluated in 10 cc of saline) was done every other day for a one week (FIG. 5). The buccal fistula was resolved by the fifth day. The buccal area of tooth #10 were wiped and isolated, and intracrevicular microbiology samples were taken for Gram staining and culture methods after one week of the topical antibiotic application (FIG. 6). The results; there was no anaerobic organisms seen, no anaerobic culture growth and no polymorphonuclear leukocytes. A chiorhexidine gluconate 0.12% oral rinse (Peridex, 3M ESPE Dental Products, St Paul, Minn.) prescribed to be used one week before and one week after the surgery.

Figure 7A:
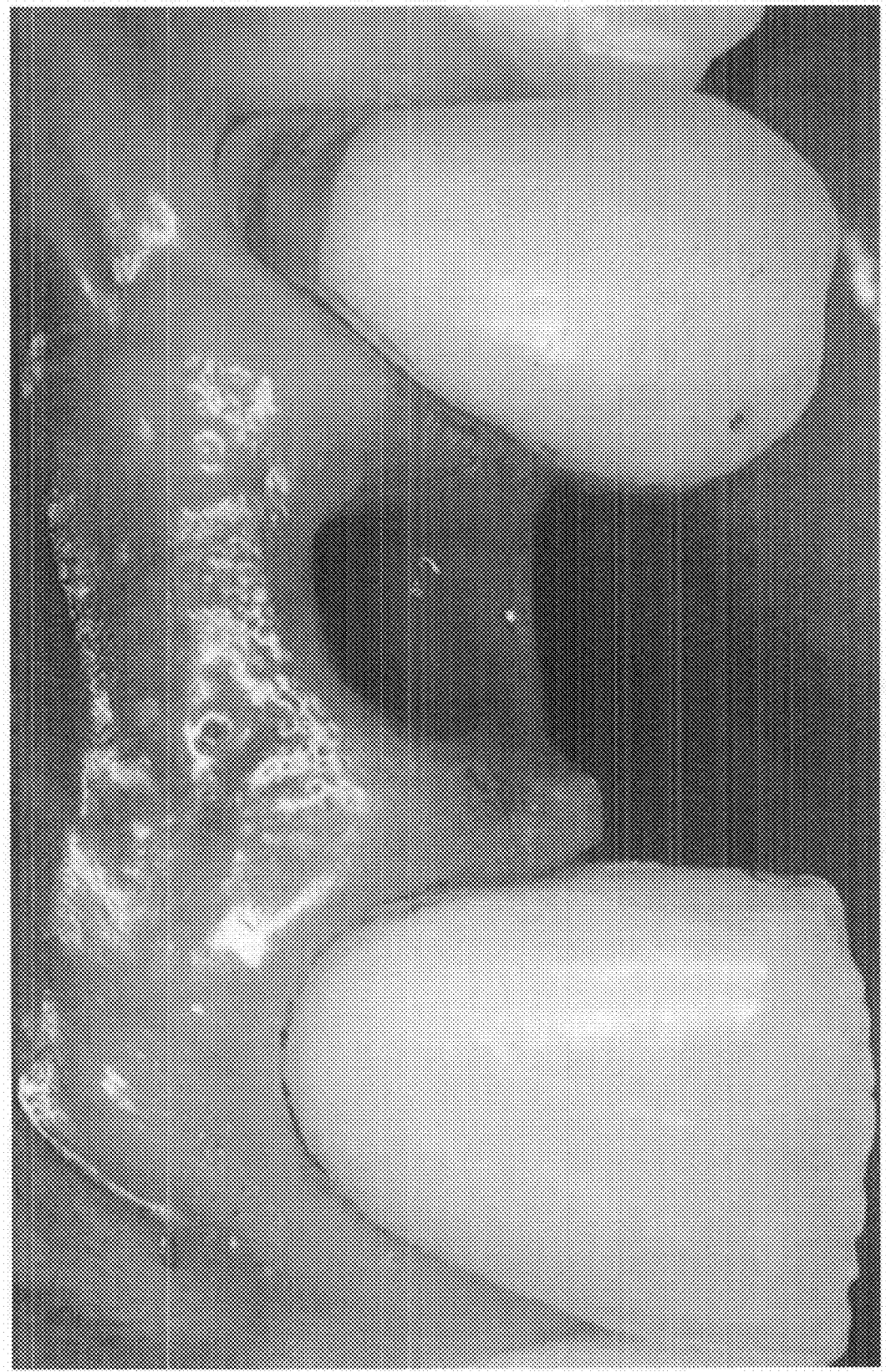
FIG. 7a: A traumatic extraction of tooth #10.
Figure 7B:
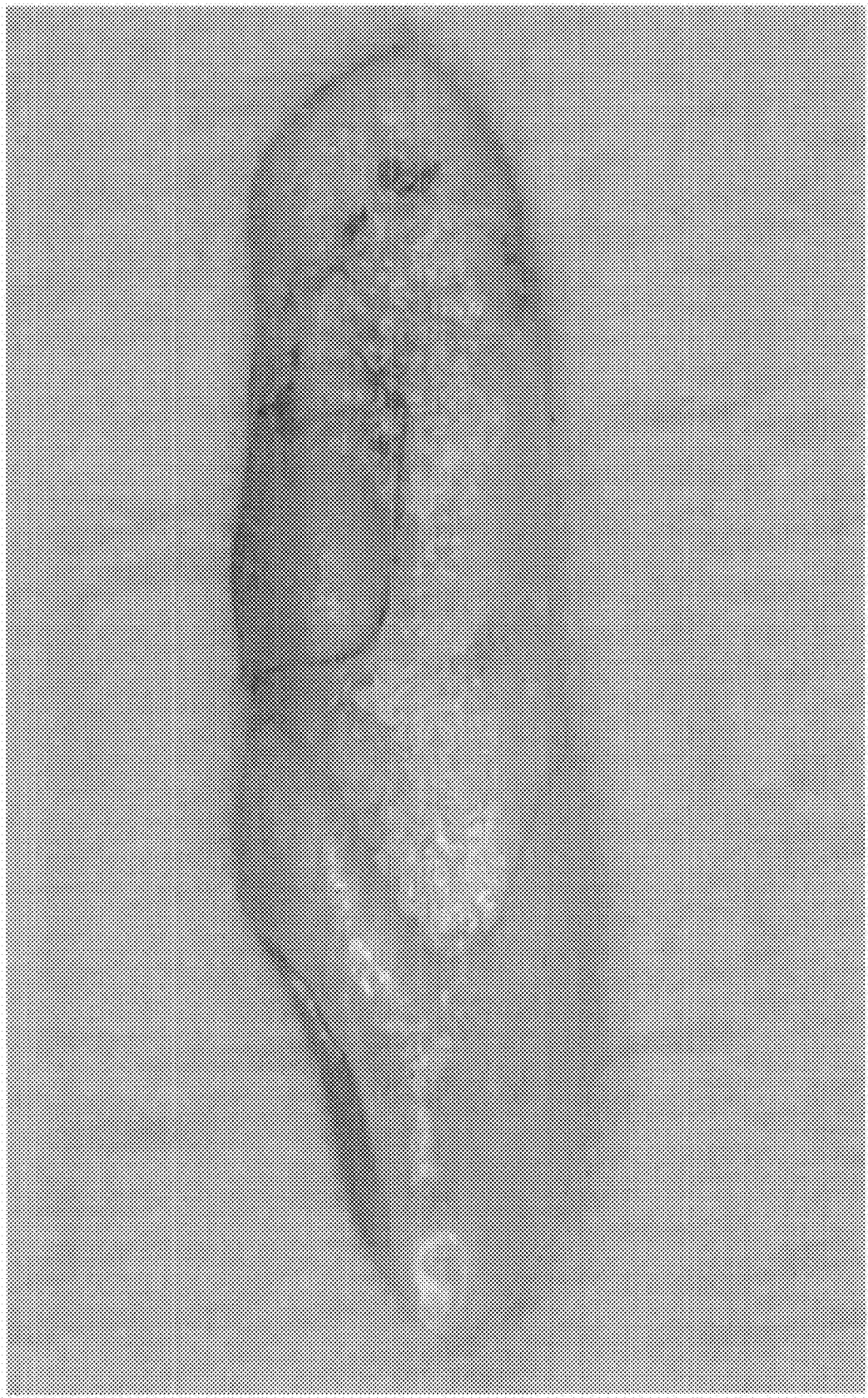
FIG. 7b: L-shaped fracture of tooth #10.
Figure 8A:
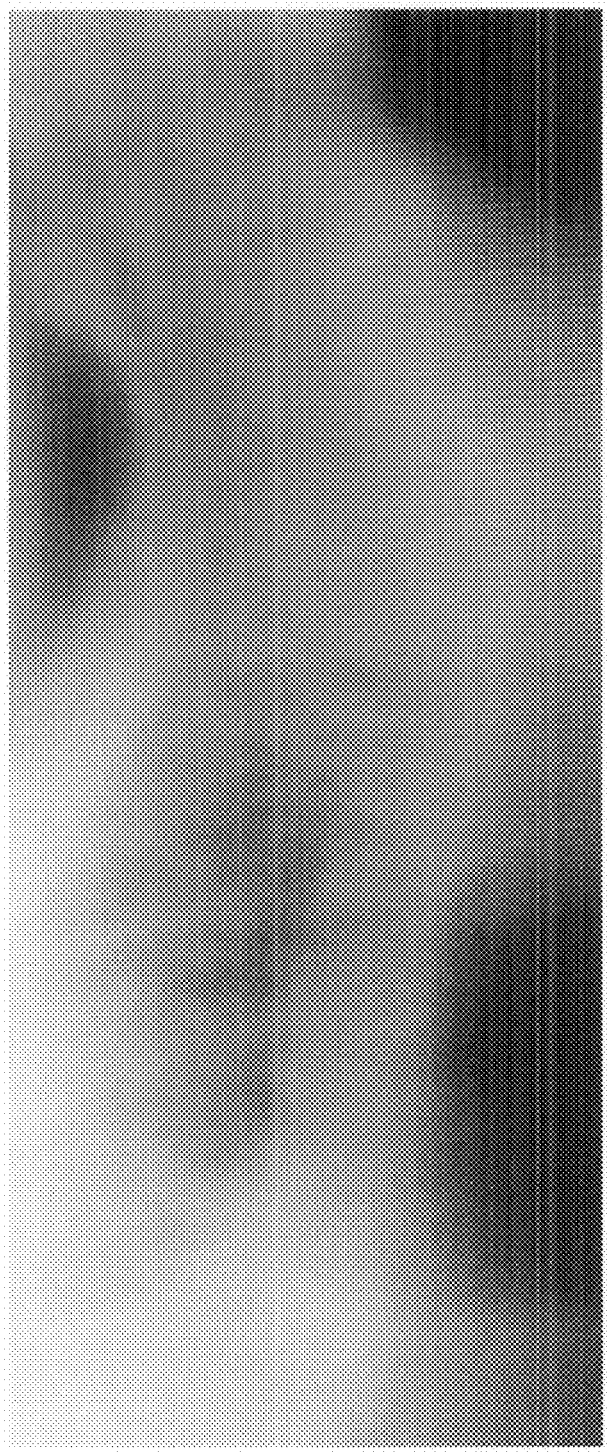
FIG. 8a: Tomographic radiograph mesial to tooth #26.
Figure 6B:
Figure 8C:
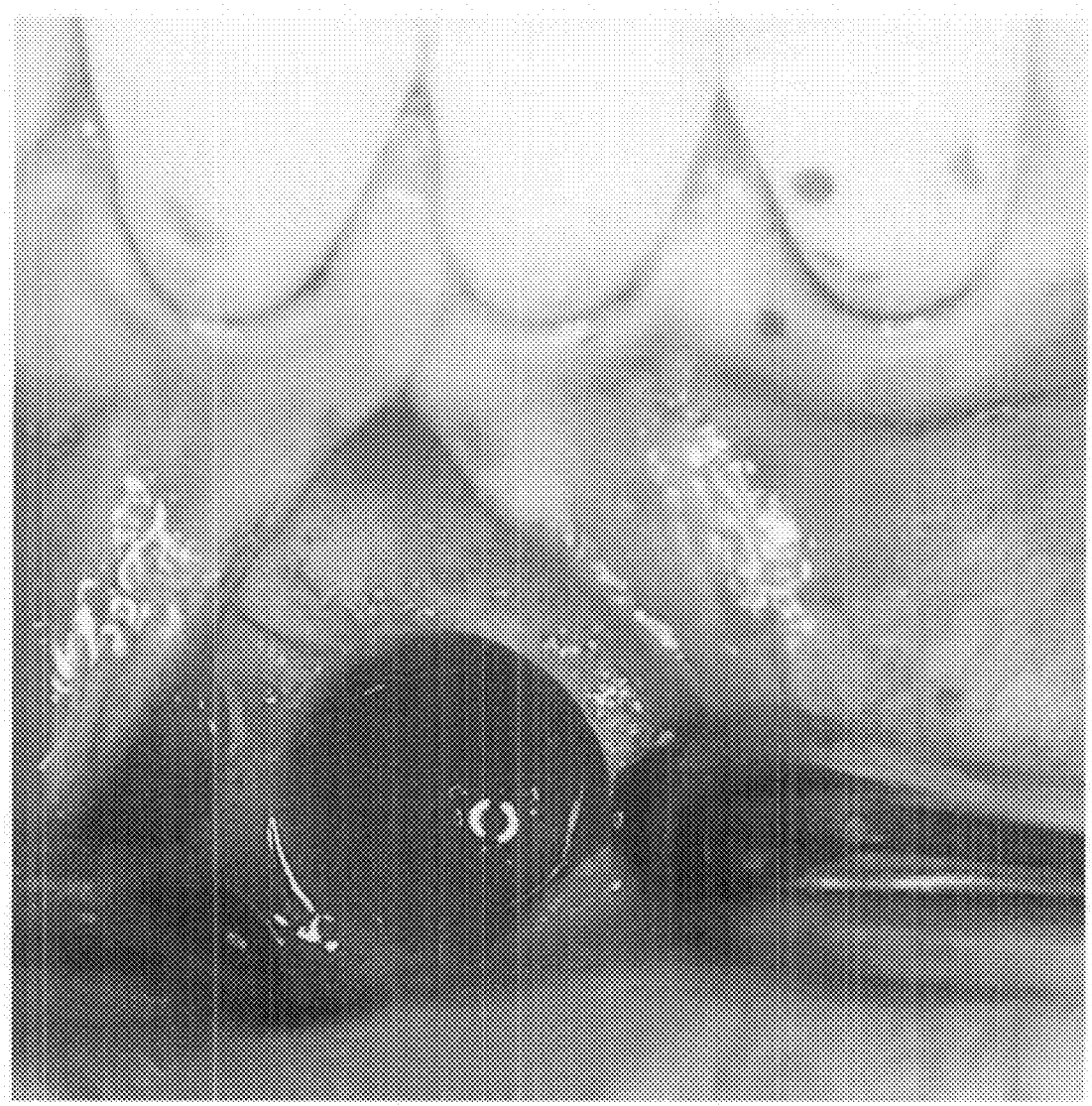
FIG. 8c: Outline of symphysis block graft.

A local anesthesia (2% Xylocaine with 1:100 000 epinephrine, Inc, New Castle, Del.) administered labially and palatally. The tooth was atraumatically extracted using the periotome, surgical elevator and surgical forceps (FIG. 7). Complete debridement of the extraction alveolus was performed and the defect size was mapped. An autogenous graft was harvested from the mandibuar symphysis area utilizing a single vertical incision beyond the mucogingival junction, apical and mesial to tooth #26 based on the tomographic and periapical radiographs using a 4.75 mm diameter trephine (FIG. 8). The donor site was filled with avitene (AVITENE Microfibrillar Collagen Hemostat; Impladent LTD) for hemostasis. The vertical incision was sutured using a resorbable material (Vicryl Sutures, Johnson & Johnson). The harvested bone was milled and prepared. Following that a mucoperiosteal flap was performed with sulcular incisions around #8, 11 and a vertical releasing incision distal to tooth #11 was performed (FIG. 9). The palatal and the interproximal bone were intact. The buccal plate was a 10 mm apical to the interproxiamal bone height.

Figure 10:
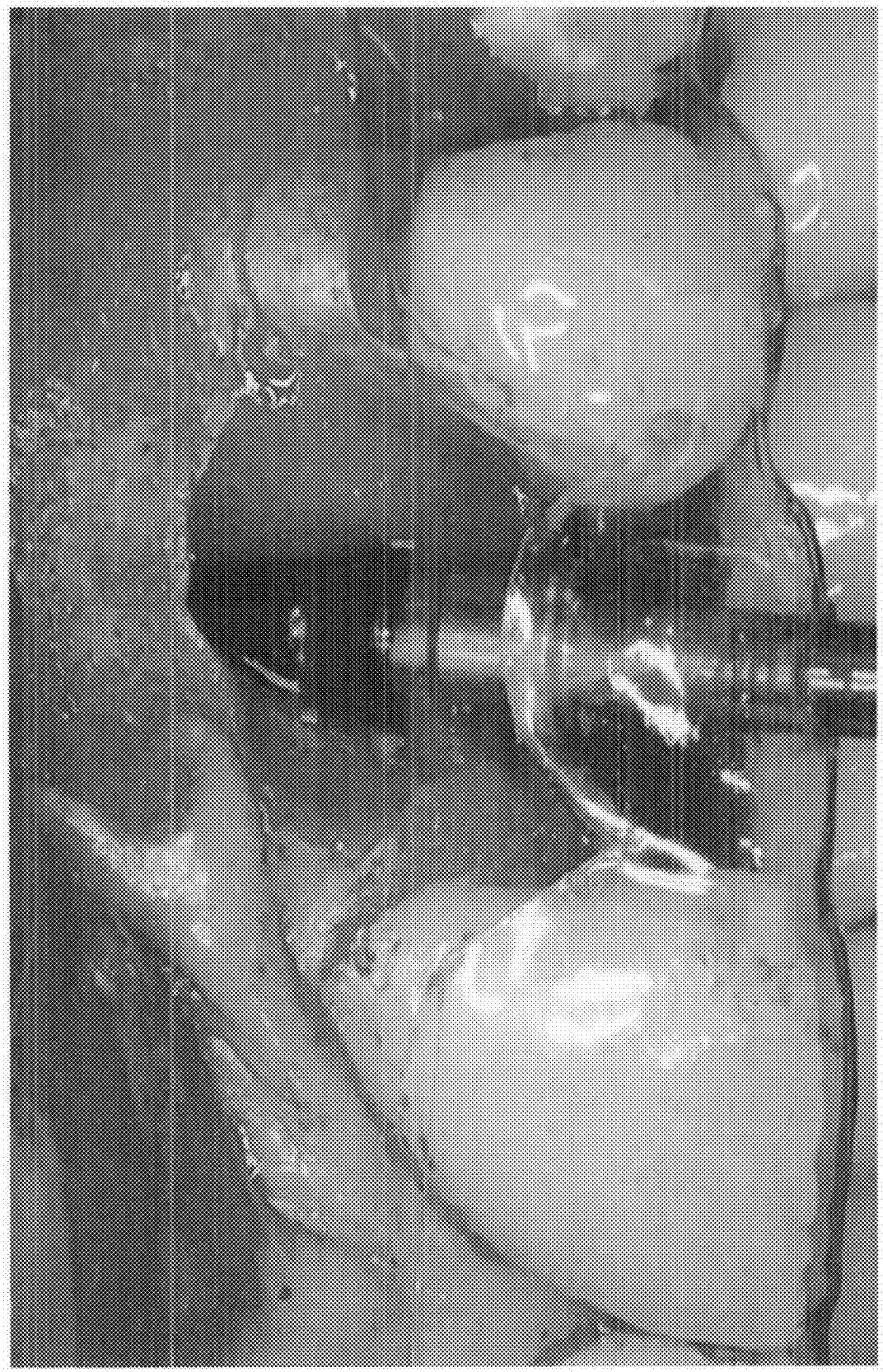
FIG. 10: Surgical procedure of implant placement with guide.
Figure 11:
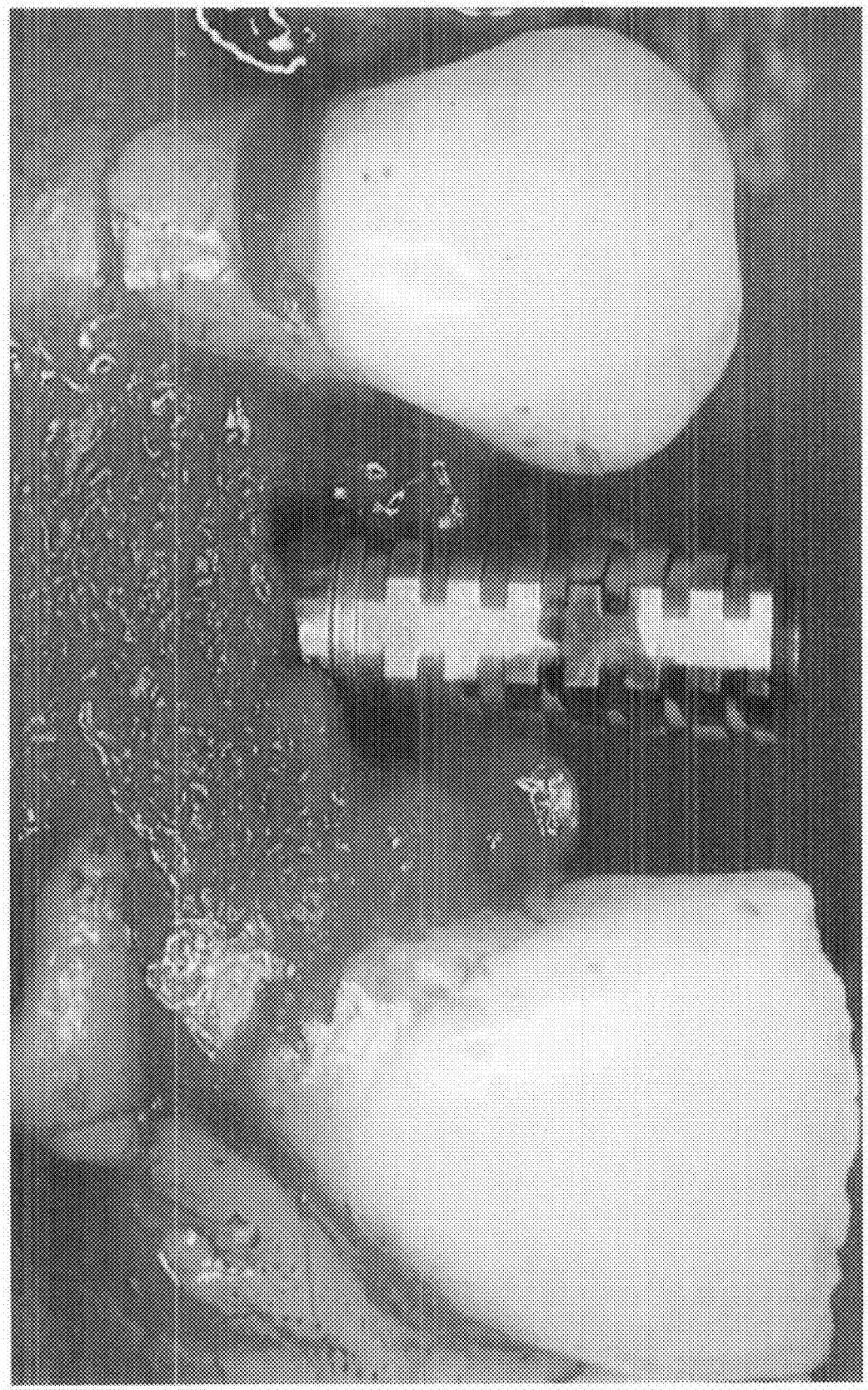
FIG. 11: Autogenous bone graft placed on the labial side cover the exposed thread.
Figure 12:
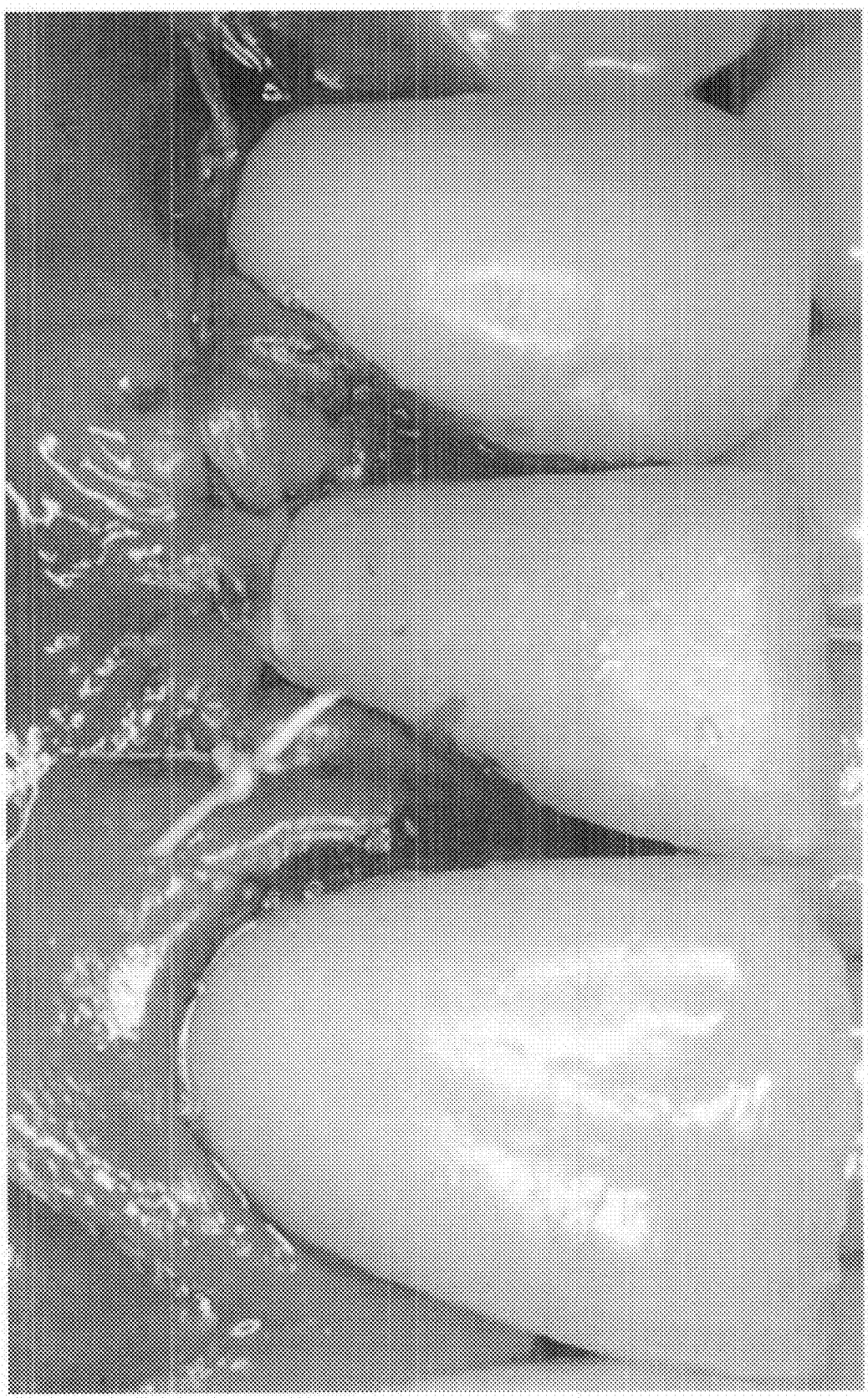
FIG. 12: The temporary abutment and crown were seated on the implant.
Figure 13:
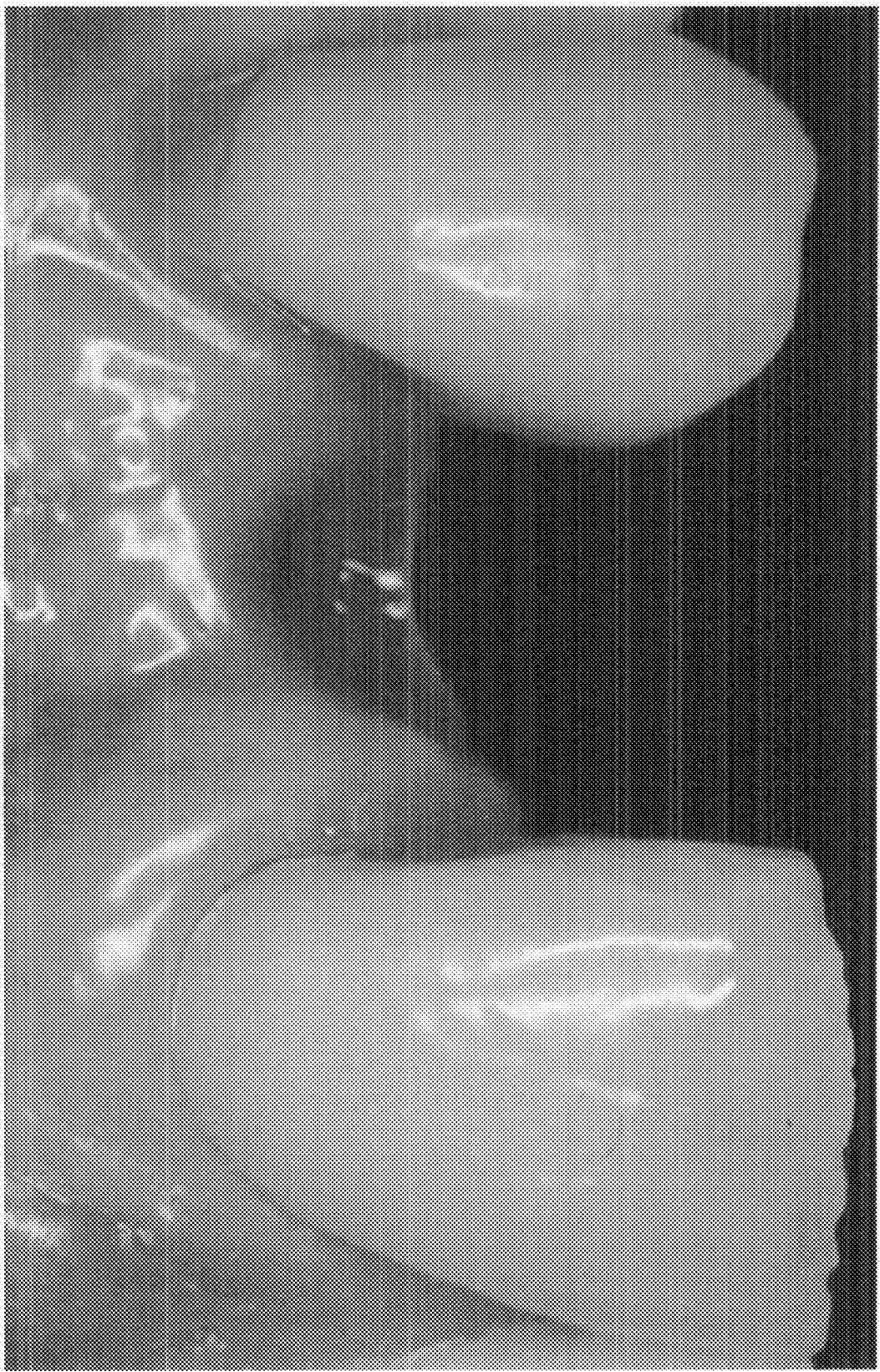
FIG. 13: Soft tissue healing 3 months after the implant placement.

The osteotomy was prepared, based on a clear form surgical template (FIG. 10). A rootform implant (NobelReplace, 3.5×16 mm) was placed. Five-implant threads were exposed on the labial side with no palatal exposure, however the implant was within the bony walls of the socket palatal to the buccal defect. A temporary abutment was placed and the particulated autogenous bone graft that was harvested from the mandibular symphysis was placed over the exposed implant threads and within the bony defect of the extraction socket for #10 (FIG. 11). A resorbable membrane (Bio-Gide, Geistlich Pharma North America) was laid over the grafted defect. A temporary abutment was hand tightened and recontoured. The coronal part of the extracted tooth was hallowed and relined using a dual cure composite material (TempSpan, C & B Material) around the temporary abutment and used as a provisional crown. The provisional crown was eliminated from centric and eccentric tooth contacts. The flap was sutured using a resorbable (Vicryl Sutures, Johnson & Johnson) and non-resorbable (Gore-Tex, Gore biomedical) material (FIG. 12) and removed two weeks post the surgery. The soft tissue healing around the implant and at the donor site was uneventful with the patient having minimal discomfort (FIG. 13).

Figure 14A:
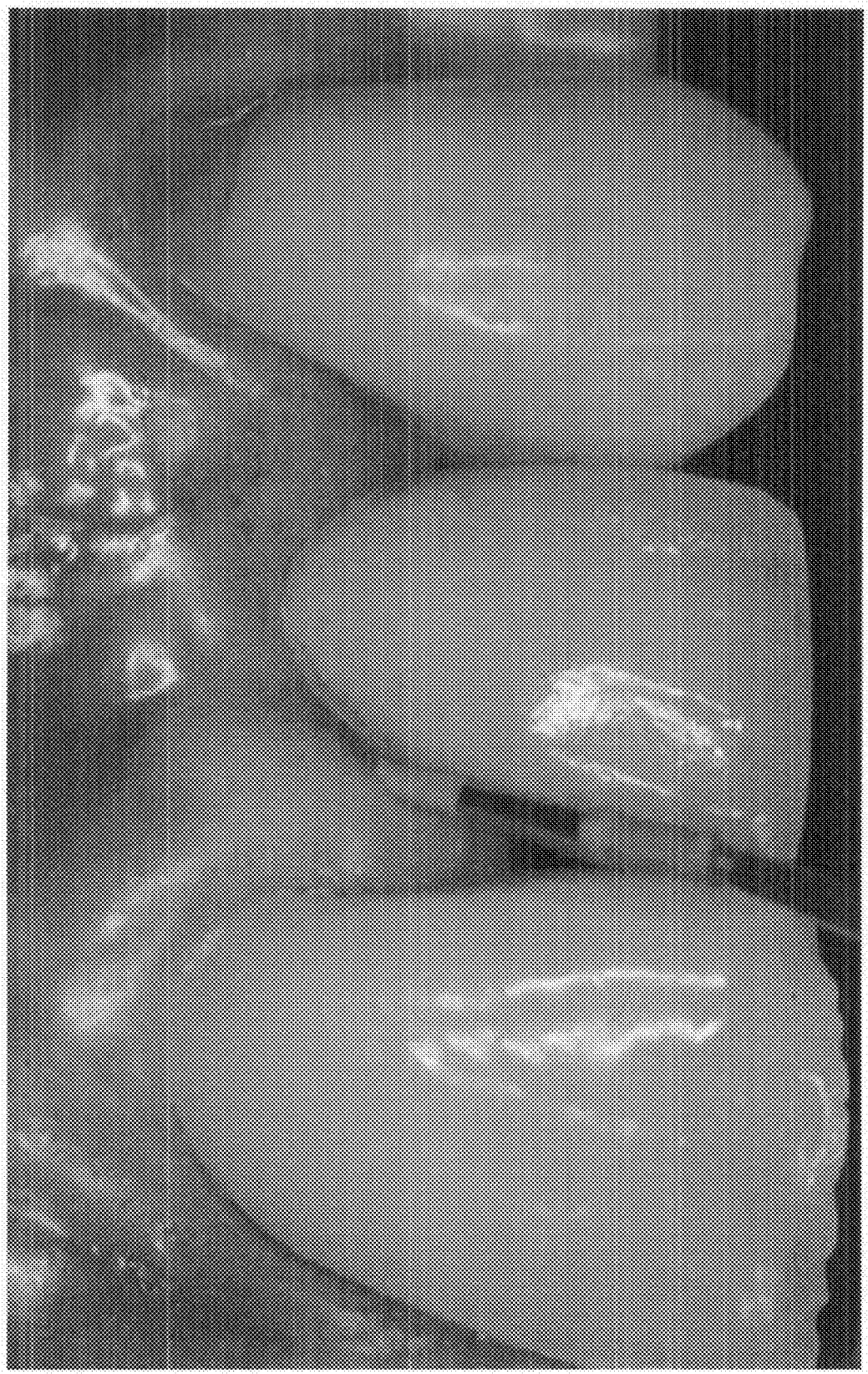
FIG. 14a: Post-treatment bone sounding, mesial of tooth #10.
Figure 14B:
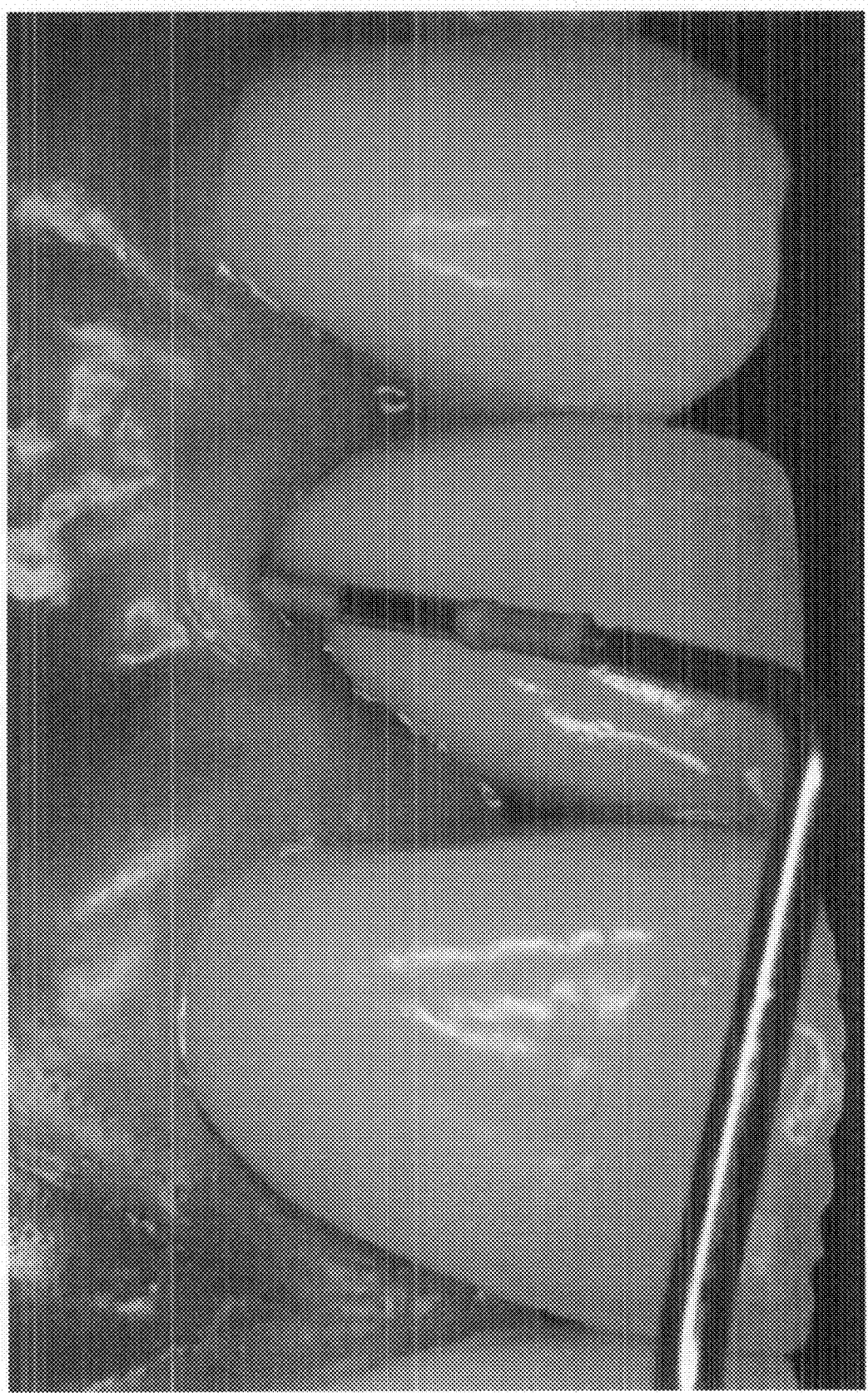
FIG. 14b: Post-treatment bone sounding, mid-buccal of tooth #10.
Figure 14C:
FIG. 14c: Post-treatment bone sounding, distal of tooth #10.
Figure 15A:
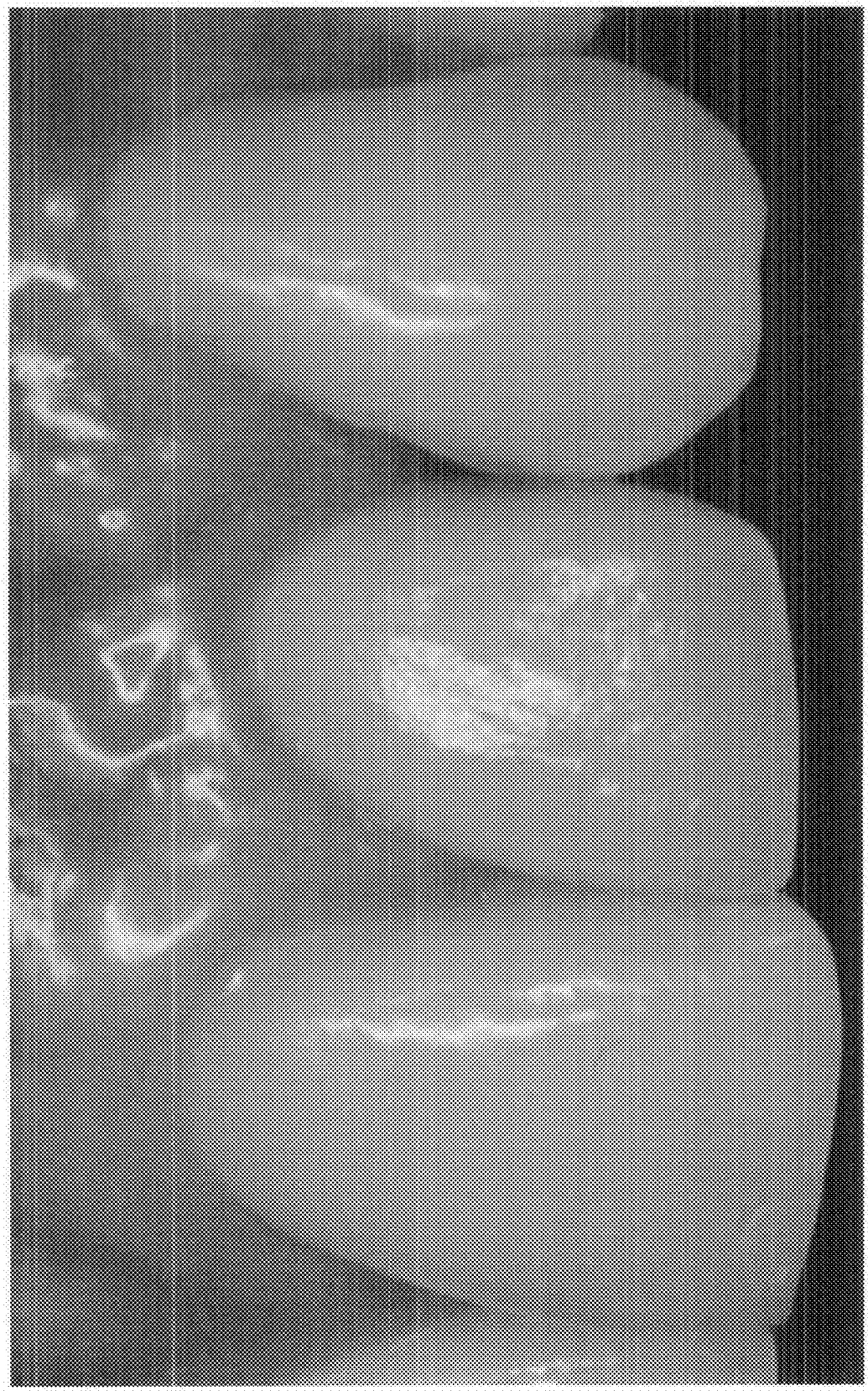
FIG. 15a: The final restoration, 6 months after implant placement of tooth #10.
Figure 15B:
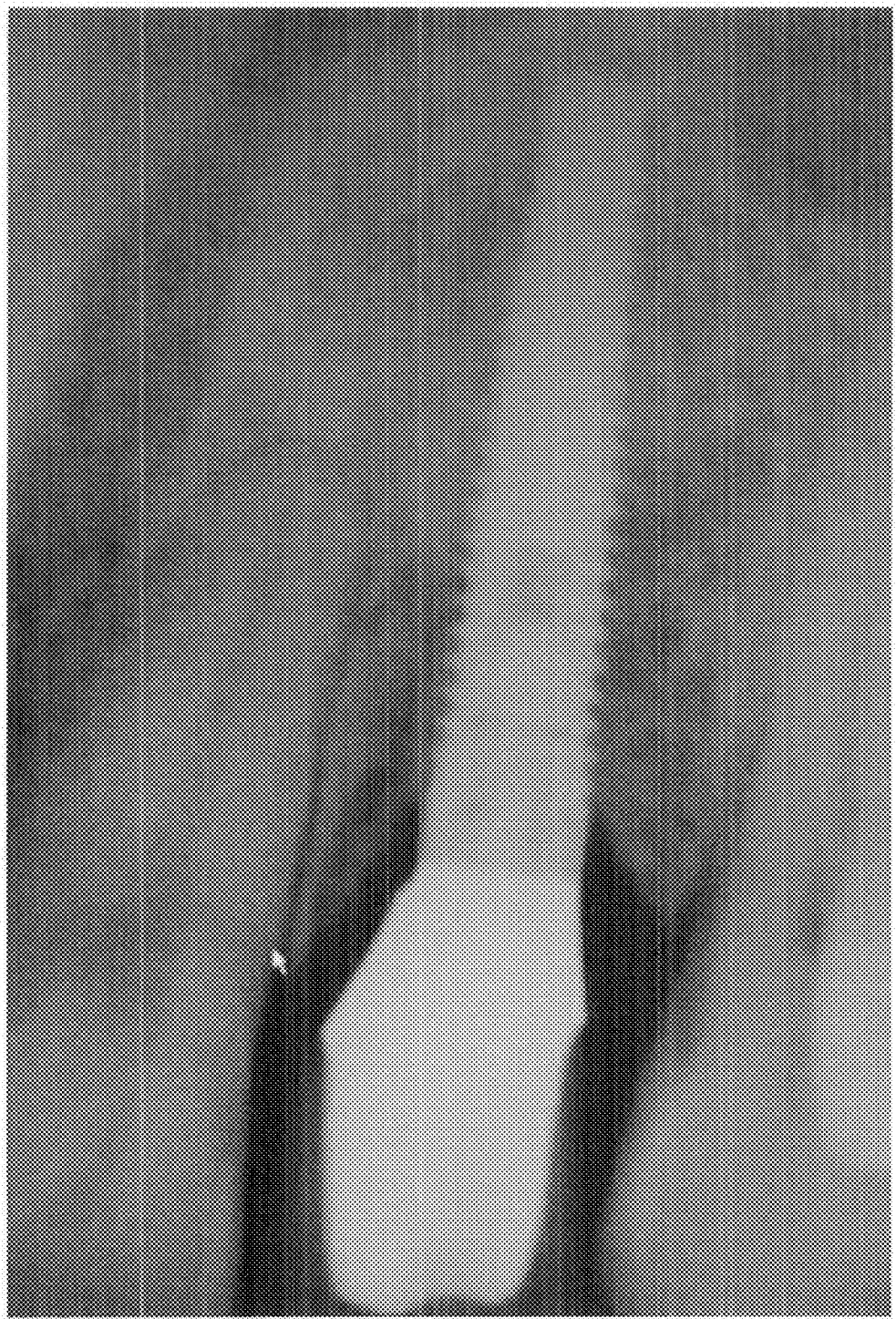
FIG. 15b: Periapical radiograph six months after the implant placement of tooth #10.

At 3 months the provisional crown discolored and was changed with a custom lab made acrylic temporary crown. The bone sounding was done after 6 months of healing as follow areas; 3 mm on distal of tooth #9, 3.5 mm on mesial of tooth #10, 3 mm on mid-buccal and 3.5 mm on distal of tooth #10; and 3.5 mm on mesial of tooth #11 (FIG. 14). A Final impression was made six months after implant placement. Custom titanium abutment (ATLANTIS™, Dentsply Implants) was fabricated. A cement retained ceramo-metal crown was processed. Temporary cement (Premier® Implant Cement™) used to cement the final crown (FIG. 15). The importance of the maintaining a high standard of oral hygiene was stressed to the patient. Tooth brushing and dental flossing technique was reinforced. Chlorohexidine (Periodex, 0.12%) mouth rinse was prescribed one time daily for seven consecutive days a month for gingival enhancement (Featherstone, J. D., Adair, S. M., Anderson, M. H., Berkowitz, R. J., Bird, W. F., Crall, J. J., Den Besten, P. K., Donly, K. J., Glassman, P., Milgrom, P., Roth, J. R., Snow, R., & Stewart, R. E., "Caries management by risk assessment: consensus statement," Journal of the California Dental Association 2002, 31(3), 257-269).

Figure 16:
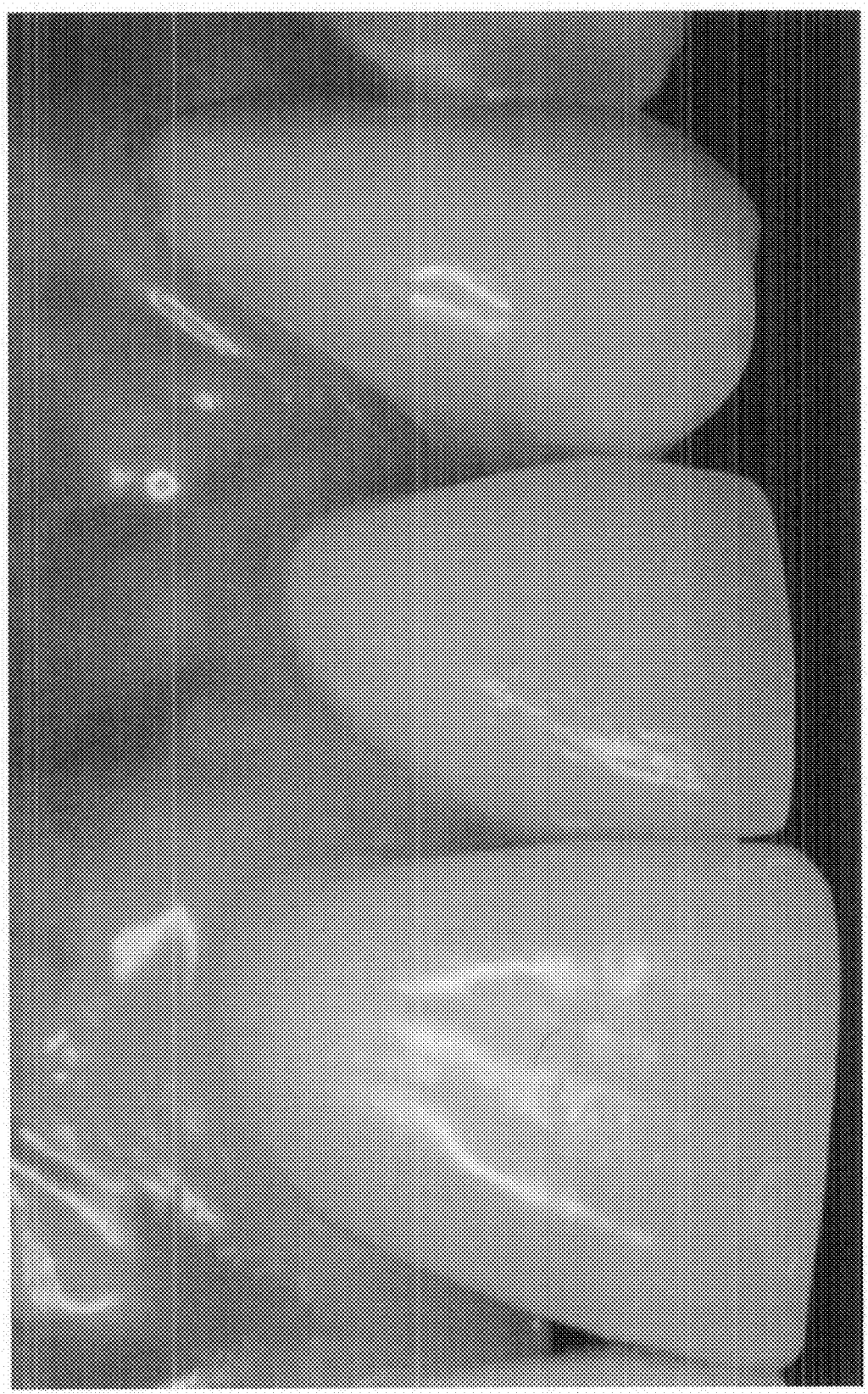
FIG. 16: The final restoration, 3 years after implant placement of tooth #10.

The prognosis was highly favorable. It was explained to the patient that the long-term prognosis of the restoration would depend on the maintenance of oral hygiene. The patient was followed up for 3 years (FIG. 16) after which she moved out of the area. There was no soft or hard tissue changes observed during the time of the follow up.

Immediate implant placement and loading was planned to maintain the soft and hard tissue complex, avoid need for additional surgeries, and shorten treatment time. Presence of an intact interproximal and palatal alveolar bone is preferred for a predictable result. Local antibiotic application was able to eliminate the pathogenic bacteria and resolve the chronic periapical abscess.

The technique described in this article utilizes a single vertical incision to harvest the bone form the symphysis area running parallel to the muscle fibers. This technique eliminates the detachment of muscles and reducing the risks of nurosensory disturbance, chin ptosis and patient discomfort. However, careful mapping of the apex of the anterior teeth is needed and compared to the classical approach the amount of harvested bone is limited to one or two trephines due to the limited access mandated by the single vertical incision.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A surgical technique for harvesting an autogenous symphysis bone graft, comprising:
    making no more than one vertical incision to the symphysis area of a patient's mandible, and
    harvesting bone from the symphysis area of the patient's mandible,
    wherein the no more than one vertical incision is made parallel to muscle fibers of the patient's chin.

2. The surgical technique of claim 1, wherein the no more than one vertical incision is made without muscular detachment in the symphysis area of the patient.

3. The surgical technique of claim 2, further comprising:
    harvesting bone from the symphysis area of the patient at the point of the no more than one vertical incision.

4. The surgical technique of claim 3, further comprising:
    inserting the harvested bone from the patient to regenerate a defected area in the oral cavity of the patient.

5. The surgical technique of claim 4, further comprising:
    suturing the site of the no more than one vertical incision.

6. The surgical technique of claim 1, wherein the no more than one vertical incision is made beyond the mucogingival junction.

7. The surgical technique of claim 1, wherein the bone is harvested from the symphysis area of the patient's mandible with a 4.75 mm diameter trephine.

8. The surgical technique of claim 1, further comprising filling the symphysis area of the patient's mandible with microfibrillar collagen hemostat for hemostasis.

9. The surgical technique of claim 1, further comprising milling and preparing the harvested bone for insertion into the oral cavity of the patient to regenerate a defected area.

* * * * *